(12) United States Patent
Ardaud et al.

(10) Patent No.: US 9,969,670 B2
(45) Date of Patent: *May 15, 2018

(54) SYNTHESIS OF (METH) ACRYLIC ANHYDRIDE BY TRANSANHYDRIZATION

(71) Applicant: RHODIA OPERATIONS, Paris (FR)

(72) Inventors: Pierre Ardaud, Saint-Foy-les-Lyon (FR); Thierry Vidal, Lyons (FR); Rabih Rached, Millery (FR)

(73) Assignee: Rhodia Operations, Paris (FR)

(*) Notice: Subject to any disclaimer, the term of this patent is extended or adjusted under 35 U.S.C. 154(b) by 0 days. days.

This patent is subject to a terminal disclaimer.

(21) Appl. No.: 15/111,258

(22) PCT Filed: Jan. 20, 2015

(86) PCT No.: PCT/EP2015/050972
§ 371 (c)(1),
(2) Date: Jul. 13, 2016

(87) PCT Pub. No.: WO2015/107210
PCT Pub. Date: Jul. 23, 2015

(65) Prior Publication Data
US 2016/0332949 A1 Nov. 17, 2016

(30) Foreign Application Priority Data

Jan. 20, 2014 (FR) .................................. 14 00106

(51) Int. Cl.
C07C 67/48 (2006.01)
C07C 51/573 (2006.01)
C07C 51/56 (2006.01)

(52) U.S. Cl.
CPC ............ *C07C 51/573* (2013.01); *C07C 51/56* (2013.01)

(58) Field of Classification Search
CPC ............................. C07C 51/573; C07C 51/56
(Continued)

(56) References Cited

U.S. PATENT DOCUMENTS 8,097,757 B2 1/2012 Paul et al.
9,266,811 B2 * 2/2016 Ardaud .................. C07C 51/56
(Continued)

FOREIGN PATENT DOCUMENTS

EP 0 196 520 A1 10/1986
EP 0196520 A1 * 10/1986 ........... C07C 51/567
(Continued)

Primary Examiner — Deborah D Carr

(57) ABSTRACT

The invention relates to a method for producing a (meth) acrylic anhydride A-C(=O)—O—(O=)C-A, comprising the following steps: a) a step of reacting an anhydride B—C(=O)—O—(O=)C—B with an acid A-COOH, resulting in the formation of mixed anhydride A-C(=O)—O—(O=)C—B and acid B—COOH; and b) a step of reacting the mixed anhydride with A-COOH, resulting in the (meth)acrylic anhydride. According to the invention, reaction steps (a) and (b) are carried out in the presence of hydrated triflic acid, and the anhydride A-C(=O)—O—(O=)C-A is isolated from the reaction medium produced in step (b) as follows: e1) heavy compounds having a volatility less than or equal to that of the anhydride A-C(=O)—O—(O=)C-A are separated from the reaction medium, said compounds including the anhydride and the hydrated triflic acid; e2) the anhydride is separated from the heavy compounds by difference in volatility.

17 Claims, 2 Drawing Sheets

(58) Field of Classification Search
 USPC .......................................................... 560/191
 See application file for complete search history.

(56) References Cited

U.S. PATENT DOCUMENTS

2002/0161260 A1 10/2002 Schmitt et al.
2009/0264673 A1 10/2009 Broell et al.

FOREIGN PATENT DOCUMENTS

GB 538 310 A 7/1941
WO 2009098422 A1 8/2009

* cited by examiner

SYNTHESIS OF (METH) ACRYLIC ANHYDRIDE BY TRANSANHYDRIZATION

This application is a U.S. national phase entry under 35 U.S.C. § 371 of International Application No. PCT/EP2015/050972, filed on Jan. 20, 2015, which claims priority to French Application No. 14/00106, filed on Jan. 20, 2014. The entire contents of these applications are incorporated herein by this reference.

The present invention relates to a process for preparing (meth)acrylic anhydride by reaction of a (meth)acrylic acid with an anhydride other than a (meth)acrylic anhydride, according to a "transanhydridization" reaction.

(Meth)acrylic anhydrides are conventionally prepared by a transanhydridization reaction, typically by reaction of (meth)acrylic acid with acetic anhydride, whereby acetic acid and the desired anhydride are formed. The acetic acid formed is generally removed by distillation as it is formed. This type of reaction, which is well known, is described, for example, in patent application EP 1 273 565.

In addition to the preparation of the desired (meth)acrylic anhydride, by-products are formed, in particular polymerization products and addition products, which necessitate purification of the (meth)acrylic anhydride formed. The content of these by-products can be reduced in a manner known per se by the addition of polymerization inhibitors. Nevertheless, even on employing such inhibitors, by-products continue to be formed. Typically, these by-products are removed by distillation, which is a problematic operation, in particular in view of the lachrymatory nature of the (meth)acrylic anhydride.

Processes for the synthesis of (meth)acrylic anhydride of batch type (noncontinuous batchwise processes) have in particular been described, for example in patent application EP 0 231 689.

Alternatively, more advantageous continuous and semicontinuous processes have also been provided, in particular in EP 1 237 565 or US 2009/0264673, and make it possible to reduce the presence of by-products.

Furthermore, it has been envisaged to use catalysts for improving the reaction. In this context, essentially, it is heterogeneous catalysts that have been envisaged, in particular in US 2002/0161260, and which can present difficulties in terms of extrapolation or of material transfer. More occasionally, homogeneous catalysts have been provided, for instance the sulfuric acid described in DE 3510035, which do not present this type of difficulty but which, in return, usually have a major drawback, namely that they generally involve burdensome post-treatment steps in order to be separated from the anhydride. Thus, these catalysts do not result systematically in an improvement in the yield and in addition often have the drawback of having to be removed on conclusion of the reaction. One aim of the present invention is to provide a process for preparing (meth)acrylic anhydride which avoids burdensome steps of post-treatment of the anhydride, in particular burdensome steps of removal of the catalyst used.

The present invention is also directed toward providing an effective process for preparing (meth)acrylic anhydride which can, if need be, be performed in a continuous mode, avoiding the burdens and drawbacks of the processes of batch type.

To this end, the present invention provides for the use of a particular catalyst, namely triflic acid in hydrated form.

In the context of the studies that led to the present invention, the inventors have revealed that triflic acid is a catalyst that is particularly advantageous for the transanhydridization reaction. The inventors have revealed that triflic acid is a particularly reactive catalyst, resulting in a short residence time in the reaction zone and allowing the implementation of the continuous process. Triflic acid also has the property, when it is anhydrous, of being more volatile than the anhydride formed in the reaction and can thus be readily separated out and recycled.

The inventors have more specifically revealed, unexpectedly, that when triflic acid is used in the presence of traces of water in the transanhydridization reaction (typically water contained in trace amount in the starting (meth)acrylic acid), triflic acid is totally or partly converted into its hydrated form (in general, triflic acid is totally converted into its hydrated form given the small amount of triflic acid used and the high reactivity of this acid).

As illustrated in the attached Example 2, triflic acid in its hydrated form has reactivity similar to that of the anhydrous form and thus remains advantageous for promoting the transanhydridization reaction. However, in contrast with triflic acid in anhydrous form, the hydrated form of triflic acid proves to be less volatile than the (meth)acrylic anhydride formed on conclusion of the reaction and therefore cannot be separated out as readily as the anhydrous form.

Nevertheless, the inventors have developed a process that is easy to perform for readily separating out methacrylic anhydride on conclusion of the reaction, said process forming the subject of the present invention.

More precisely, the present invention proposes a process for preparing an anhydride of formula A-C(=O)—O—(O=)C-A in which A is a group —CH=CH$_2$ or —C(CH$_3$)=CH$_2$, said process comprising:

a) a step of reacting an anhydride B—C(=O)—O—(O=)C—B with an acid A-COOH, A being as defined above, this step leading to the formation of an anhydride A-C(=O)—O—(O=)C—B and of an acid B—COOH, A and B being such that said acid B—COOH is more volatile than said acid A-COOH; and b) a step of reacting said anhydride A-C(=O)—O—(O=)C—B with the acid A-COOH under conditions such that the amount of acid B—COOH is less than the amount of acid A-COOH, resulting in the formation of the anhydride A-C(=O)—O—(O=)C-A, in which:

said steps (a) and (b) are performed in the presence of triflic acid in hydrated form the anhydride A-C(=O)—O—(O=)C-A formed in step (b) is isolated from the reaction medium derived from step (b) according to the following successive or concomitant separation steps:

e1) the "heavy" compounds, having a volatility less than or equal to that of the anhydride A-C(=O)—O—(O=)C-A, are separated from said reaction medium, typically by fractional distillation, these heavy compounds including the anhydride A-C(=O)—O—(O=)C-A and triflic acid in hydrated form;

e2) the anhydride A-C(=O)—O—(O=)C-A is separated from the heavy compounds by difference in volatility.

In the context of the present description, the term "(meth)acrylic" is employed in the present description as being synonymous with the expression "acrylic and/or methacrylic". Thus, when reference is made to a (meth)acrylic acid, this term denotes acrylic acid $CH_2$=CH—COOH or methacrylic acid $CH_2$=C(CH$_3$)—COOH or alternatively a mixture of these two acids. In the same way, if reference is made to a (meth)acrylic anhydride, the intention is to denote an acrylic anhydride $CH_2=CH—C(=O)—O—(O=)C—CH=CH_2$, a methacrylic anhydride $CH_2=C(CH_3)—C(=O)—O—(O=)C—C(CH_3)=CH_2$, a mixed acrylic and methacrylic anhydride $CH_2=CH—C(=O)—O—(O=)C—C(CH_3)=CH_2$ or else a mixture of these anhydrides.

The process of the invention makes it possible to prepare the various species corresponding to the term "(meth)acrylic anhydride", namely, acrylic anhydride, methacrylic anhydride or a mixture of the two, as a function of the choice of the acid A-COOH employed in the process.

According to an advantageous embodiment, the (meth)acrylic anhydride prepared according to the invention is either an acrylic anhydride $CH_2=CH—C(=O)—O—(O=)C—CH=CH_2$ or a methacrylic anhydride $CH_2=C(CH_3)—C(=O)—O—(O=)C—C(CH_3)=CH_2$, respectively starting from acrylic acid or methacrylic acid as acid A-COOH. However, it is not ruled out, according to a more particular embodiment, to start from a mixture of acrylic and methacrylic acids.

According to the invention, the process for preparing (meth)acrylic anhydride comprises a step, denoted a), of reacting an anhydride B—C(=O)—O—(O=)C—B with triflic acid in hydrated form.

For the purposes of the present invention, the term "triflic acid in hydrated form" denotes triflic acid bound to water. Triflic acid in hydrated form, which forms when the acid is placed in contact with water, behaves like a defined compound, different from triflic acid and differing therefrom especially by a lower volatility than that of triflic anhydride.

The choice of an anhydride B—C(=O)—O—(O=)C—B such that B—COOH is more volatile than A-COOH has the effect that each of the products which can be formed during the reaction step is more volatile than the (meth)acrylic anhydride A-C(=O)—O—(O=)C-A. The latter, which is less volatile, is then generally easier to isolate from the remainder of the compounds present, during subsequent treatment steps.

This step a) leads to the formation of a compound of mixed anhydride type A-C(=O)—O—(O=)C—B, which is more volatile than the anhydride A-C(=O)—O—(O=)C-A, and of an acid B—COOH.

According to the invention, the process for preparing the (meth)acrylic anhydride also comprises a step, denoted b), of reacting said anhydride A-C(=O)—O—(O=)C—B with the acid A-COOH under conditions such that the amount of acid B—COOH is less than the amount of acid A-COOH.

Under such conditions, step b) leads to the formation of the anhydride A-C(=O)—O—(O=)C-A.

This is because, when the amount of acid B—COOH is less than the amount of acid A-COOH, the reaction equilibrium tends toward the formation of the desired anhydride. Thus, the mixed anhydride A-C(=O)—O—(O=)C—B reacts with the acid A-COOH, leading to the formation of the anhydride A-C(=O)—O—(O=)C-A and of acid B—COOH.

If such conditions are not adhered to, then the mixed anhydride cannot react with the acid A-COOH to form the anhydride A-C(=O)—O—(O=)C-A; it may thus be found among the final products.

Thus, during the process, when the amount of acid B—COOH becomes greater than the amount of acid A-COOH, the second reaction step can no longer take place. Both anhydride A-C(=O)—O—(O=)C-A and mixed anhydride A-C(=O)—O—(O=)C—B are then obtained among the final products. The fact that the mixed anhydride A-C(=O)—O—(O=)C—B is more volatile than the anhydride A-C(=O)—O—(O=)C-A allows it to be readily separated therefrom.

In the context of the invention, the reaction steps a) and b) can take place simultaneously or sequentially.

The two combined reaction steps a) and b) of the process according to the invention may be referred to as the "transanhydridization reaction".

Thus, the (meth)acrylic anhydride is formed according to a transanhydridization reaction, i.e. starting from the (meth)acrylic acid and from an anhydride B—C(=O)—O—(O=)C—B different from the desired anhydride and leading to the desired (meth)acrylic anhydride and a carboxylic acid B—COOH different from the initial acid, with the anhydride A-C(=O)—O—(O=)C—B as intermediate compound between the initial and final anhydrides.

It is possible to associate, with this transanhydridization reaction, a reaction region which delimits the space in which the two steps a) and b) take place.

Thus, different compounds can be present in the reaction region and on exiting this region.

More specifically, at a given instant, the reaction region generally comprises anhydride B—C(=O)—O—(O=)C—B, acid A-COOH, the catalyst, the mixed compound A-C(=O)—O—(O=)C—B, acid B—COOH and anhydride A-C(=O)—O—(O=)C-A. All of these compounds may also be present on exiting the reaction region.

This is because, as indicated above, the reagents B—C(=O)—O—(O=)C—B and A-COOH, and also the catalyst, react in the reaction region to form first the mixed anhydride A-C(=O)—O—(O=)C—B and the acid B—COOH. Next, if the amount of acid B—COOH is less than that of acid A-COOH, the mixed anhydride then reacts with the acid A-COOH and anhydride A-C(=O)—O—(O=)C-A is formed.

According to the invention, the anhydride B—C(=O)—O—(O=)C—B and the acid A-COOH are more volatile than the anhydride prepared. The anhydride formed is thus less volatile than the reagents, which facilitates its isolation, even when a certain amount of reagents have not reacted and are found among the compounds formed during the reaction.

Thus, the anhydride B—C(=O)—O—(O=)C—B, the acid A-COOH and the acid B—COOH are more volatile than the anhydride A-C(=O)—O—(O=)C-A formed. The anhydride formed, and the heavier triflic acid, are thus the least volatile compounds among the products and reagents (they constitute the heavy fraction, which is easy to separate from the other reaction products, reagents and intermediates). Separating the anhydride out from this heavy fraction may thus be readily performed via the separation steps (e1) and (e2).

According to a first embodiment, steps (e1) and (e2) are performed successively, i.e. by separating out the heavy compounds in step (e1) and treating these heavy compounds downstream in the separation step (e2) to extract the desired anhydride. In this case, step (e2) is typically performed downstream of step (e1), using a distillation column or using apparatus with a short residence time such as a falling-film evaporator or a scraped-film evaporator. Step (e2) may be performed, for example, in a short-path device of the type described in U.S. Pat. Nos. 3,434,935 or 4,517,057.

According to another possible embodiment, steps (e1) and (e2) may be performed simultaneously, typically in the same distillation column in which the compounds other than the heavy compounds are extracted at the top of the column and the heavy compounds at the bottom part, by separately withdrawing:

in the lowest part of the column:
the heaviest compounds, including hydrated triflic acid
in a higher part:
meth(acrylic) anhydride.

In one possible variant of the invention, which is compatible with the various modes envisaged above in the present description, the acid B—COOH is removed during steps a) and b).

This removal of the acid B—COOH may be performed, for example, by distillation.

As mentioned above, during step b), the mixed anhydride A-C(=O)—O—(O=)C—B can react with the acid A-COOH to give the desired anhydride A-C(=O)—O—(O=)C-A, if the amount of acid B—COOH is less than that of acid A-COOH. Consequently, in order to obtain such conditions and to shift the reaction equilibrium toward the formation of the desired anhydride, the acid B—COOH formed can be removed during steps a) and b), i.e. withdrawn from the reaction region.

Gradual removal of the acid B—COOH thus makes it possible to obtain conditions allowing the formation of the desired anhydride A-(C=O)—O—(C=O)-A.

According to a particular embodiment, which is compatible with the preceding embodiments, steps (a) and (b) of the process are performed continuously.

In the context of the present description, the term "process performed continuously" or more simply "continuous process" means a process in which the various successive operations follow on from each other without interruption and consequently in which the product, in this instance (meth)acrylic anhydride, is produced uninterruptedly.

Thus, according to this embodiment, the reagents are introduced continuously and the compounds liable to be obtained are also recovered continuously. The process of the invention can thus either be performed noncontinuously and is then termed a "batch process" or "batchwise process" or can be performed continuously and is then termed a "continuous process".

According to an advantageous embodiment of the invention, which is also compatible with all the preceding embodiments, the molar mass of B is less than the molar mass of A. In this context, B is preferably a methyl or ethyl group, advantageously a methyl group.

Thus, the preparation of the (meth)acrylic acid may typically be performed by reacting a (meth)acrylic acid with acetic anhydride. For example, methacrylic acid may be prepared by reacting methacrylic acid with acetic anhydride The working temperature is preferably chosen so as to obtain sufficiently rapid kinetics, while at the same time avoiding excessive degradation of the compounds. To obtain sufficiently rapid kinetics, the working temperature of steps (a) and (b) is preferably greater than 60° C., for example at least 70° C., or even at least 90° C. To avoid the temperature degrading the compounds, it is, however, preferable to perform steps (a) and (b) at a temperature that remains less than or equal to 120° C., advantageously less than or equal to 110° C., for example less than or equal to 100° C.

According to an advantageous embodiment, the reaction steps a) and b) are performed at a pressure of from 0.01 bar to 3 bar, advantageously from 0.5 bar to 1.5 bar, preferably at atmospheric pressure. For the purposes of the present invention, the term "atmospheric pressure" means the ambient pressure prevailing under the conditions of the process, equal to 1 bar or in the region of 1 bar.

The process may be performed irrespective of the pressure, but it is particularly advantageous to work at atmospheric pressure, given that this makes it possible to dispense with any pressure control.

Advantageously, the mole ratio between the acid A-COOH and the anhydride B—C(=O)—O—(O=)C—B is from 0.5 to 5, advantageously from 1.5 to 3. Preferably, this mole ratio A-COOH:B—C(=O)—O—(O=)C—B remains less than 2.5 and more preferentially less than 2.

Advantageously, the ratio of the weight of acid catalyst to the total weight of the reagents B—C(=O)—O—(O=)C—B and A-COOH is from 5 ppm to 1%, advantageously from 20 ppm to 100 ppm.

According to one embodiment, the process comprises a step of extracting the acid catalyst and the acid B—COOH formed, in order to separate out the acid catalyst and the acid B—COOH, in particular by distillation. This extraction step then takes place after steps a) and b).

On conclusion of the transanhydridization reaction, the main compounds present are the acid catalyst, the acid B—COOH and the anhydride A-C(=O)—O—(O=)C-A. Thus, the acid catalyst and the acid B—COOH formed are extracted, in particular by distillation, in order to isolate the anhydride A-C(=O)—O—(O=)C-A and to recycle, if appropriate, the catalyst in order for it to be reusable. In this case, the catalyst may be reused in the abovementioned reaction step.

It is thus possible to define an extraction region delimiting the space in which the extraction step takes place. The reaction and extraction regions may be separate, be coincident or overlap, as described later.

Advantageously, after the extraction step, the acid catalyst is recovered and recycled in order to be used in the step of reacting the acid A-COOH with the anhydride B—C(=O)—O—(O=)C—B.

Various treatments for recovering the catalyst in the catalyst/acid B—COOH mixture extracted after the reaction step may be envisaged. Preferably, the recovery of the catalyst is performed by distillation.

As indicated above, when the acid catalyst is less volatile than the acid B—COOH, separation between the catalyst and the acid B—COOH is easier. This separation is typically performed by distillation.

The reaction steps are generally performed in a reactor. This reactor then defines the reaction region. It is generally a plug-flow reactor or a stirred continuous reactor (typically of perfectly stirred type), or alternatively a cascade of stirred continuous reactors.

Advantageously, the extraction step is performed in a distillation column.

This column then defines the extraction region.

The column has, for example, from 10 to 30 theoretical plates, for example 25 to 30 theoretical plates.

As a result of the differences in volatility between the various compounds obtained, the heaviest products, namely triflic acid in hydrated form and the (meth)acrylic anhydride, are recovered at the bottom of the column, whereas the acids B—COOH are recovered at the top of the column.

According to one embodiment, the reaction steps a) and b) are performed in a reactor and the extraction step is performed in one or more successive distillation columns separate from the reactor.

Thus, the various reagents, namely B—C(=O)—O—(O=)C—B, A-COOH and the catalyst, react within the reactor, in the reaction region, to form the anhydride A-C(=O)—O—(O=)C—B, the acid B—COOH and the desired (meth)acrylic anhydride quantitatively, if the required conditions are adhered to. Since the reactor is connected to the distillation column, as steps a) and b) take place in the reactor, the various products (A-C(=O)—O—(O=)C-A, B—COOH and possibly A-C(=O)—O—(O=)C—B) and/or the reagents migrate toward the distillation column, defining the extraction region, which makes it possible to separate the anhydride formed from the other compounds present.

The reactor and the column are then separate entities.

Thus, even if the reactor is separate from the column, when the two entities are connected, the transanhydridization reaction can also take place in the column. The reaction and extraction regions are thus then initially separate, but can overlap.

The advantage of this embodiment lies in the possibility of choosing the reaction parameters within the reactor (such as the temperature, the pressure or the amounts of reagents) independently of the separation conditions in the column.

According to one advantageous embodiment, one or more polymerization inhibitors may be introduced during the process in order to limit the formation of by-products, such as polymers based on (meth)acrylic acid and/or on (meth)acrylic anhydride.

They can then be introduced with the acid A-COOH into the reaction region and/or into the extraction region.

Advantageously, these inhibitors are introduced into the extraction region. This is because they are particularly effective in the extraction region and make it possible in particular to prevent the condensation reactions liable to take place therein.

Preferably, when the extraction region consists of a distillation column, the inhibitors are introduced into the top of the column.

These inhibitors must, where appropriate, be active with regard to the polymerization while being inert with regard to the (meth)acrylic anhydrides and acid. They may in particular be chosen from hydroquinone, hydroquinone monomethyl ether, topanol A, phenothiazine and hydroxytetramethylpiperidinoxyl (hydroxy-TEMPO).

The invention is further illustrated by the description which follows, given solely by way of example and made with reference to the appended drawings, in which.

Figure 1:
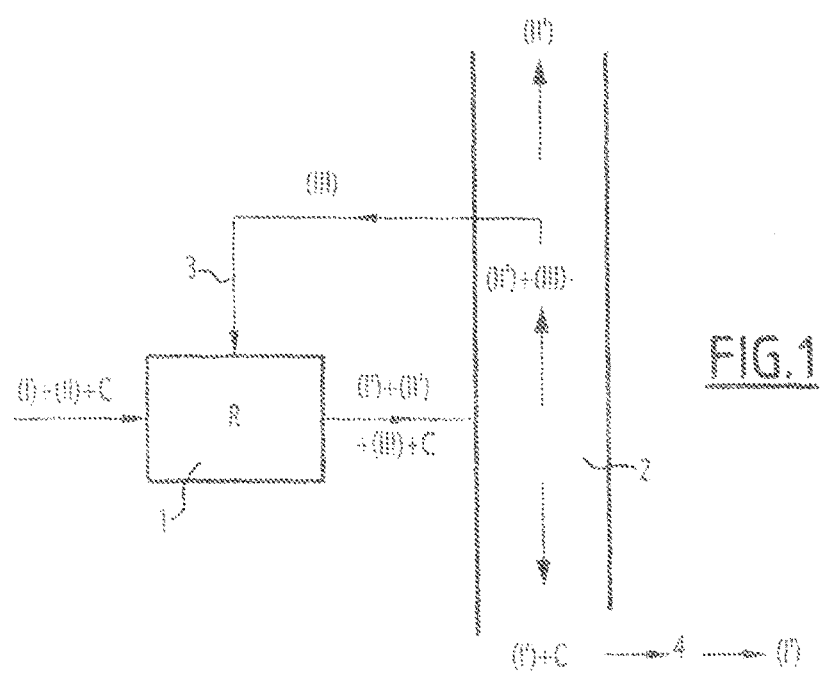
FIG. 1 is a schematic view in cross section along a median vertical plane of a first type of device suitable for performing the process of the invention in a continuous mode with implementation of step (e2) downstream of step (e1), of the type employed in Example 1 below.
Figure 2:
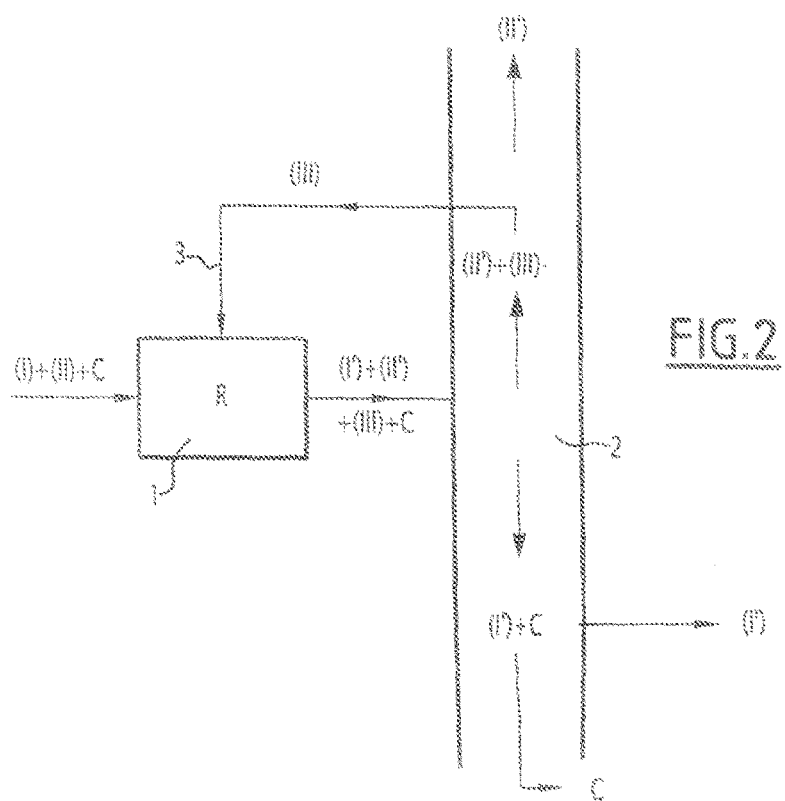
FIG. 2 is a schematic view in cross section along a median vertical plane of a second type of device suitable for performing the process of the invention in a continuous mode, for concomitant implementation of the separation steps (e1) and (e2).

The devices represented in FIGS. 1 and 2 are similar devices which differ only in the means employed for separating the anhydride formed. These devices comprise a reactor 1, typically a reactor of perfectly stirred type, or of plug-flow type, in fluid connection with an intermediate region of a distillation column 2, the top part of which is also preferably in fluid connection with the reactor 1, via a reinjection loop 3. The reinjection loop is optional but strongly recommended in practice, this loop allowing an improvement in the yield.

The process of the invention is typically performed under the following conditions in the devices of FIGS. 1 and 2:

Anhydride B—C(=O)—O—(O=)C—B, for example acetic anhydride, denoted by the general reference (I) in the figures, (meth)acrylic acid A-COOH, denoted by the general reference (II), and triflic acid, denoted C are injected continuously into reactor 1. Triflic acid is used in hydrated form, which may be obtained, for example, by using (meth)acrylic acid comprising traces of water. Other compounds may also be introduced into the reactor, for instance polymerization inhibitors.

Step a) then takes place in a reaction region of the reactor, denoted R, and leads to the formation of mixed anhydride A-C(=O)—O—(O=)C—B, denoted (III), and acid B—COOH, denoted (II'), which is typically acetic acid.

In order for step b) to be able to take place, the acid (II') is removed as it is formed in order for its amount in the region R to be less than that of the acid (II). Step b) then takes place in the region R and leads to the formation of the anhydride (I').

To do this, at the outlet of the reactor 1, the reagents (I), (II) and C, the intermediate compound (III) and the products (I') and (II') are conveyed to the distillation column 2. The heaviest products, including the anhydride (I') and triflic acid in hydrated form (and the polymerization inhibitors, where appropriate), migrate to the bottom of the column whereas the lightest compounds are entrained toward the top. The acid (II'), which is the lightest compound, migrates to the top of the column, where it is totally or partly extracted (generally, virtually all of the acid (II') is recovered at the top of the column, and the remainder of the light compounds, the mixed anhydride (III), unreacted reagents (I) and (II), and possibly acid (II') in small amount, is extracted lower down than the top of the column, to be reinjected into the reactor 1 by means of the loop 3.

The anhydride (I') is recovered from the heavy compounds that migrate toward the bottom of the column according to two possible modes:

FIG. 1 illustrates a two-step mode: the heavy compounds are all recovered at the bottom of the column (step e1) and are then separated in a device 4 in which is performed a separation of the anhydride (I'), which is the lightest of the heavy compounds (step e2). The device 4 may typically be a distillation column (in which the anhydride (I') is recovered at the top of the column), or any other device that is suitable for separating out the most volatile compound of a mixture, such as a falling-film evaporator or a scraped-film evaporator.

FIG. 2 illustrates a one-step mode: separation of the heavy compounds is performed in the bottom part of the column, by recovering the heaviest compounds at the bottom of the column and extracting therefrom the anhydride (I') higher up than the bottom of the column.

It should be noted that FIGS. 1 and 2 represent two particular embodiments that are not limitations of the invention.

Other variants may be implemented. For example, the separation performed in a single distillation column in the devices of FIGS. 1 and 2 may, alternatively, be performed in successive columns.

Thus, for example, instead of separating out the most volatile compounds in the column 2, it may be envisaged to place the top part of the column 2 in fluid connection with a second column (not shown in the figures) and to recover the acid (I') at the top of this second column and the other compounds at the bottom of the second column, to return these other compounds to the reactor 1.

EXAMPLES

Example 1

Preparation of Methacrylic Anhydride According to the Invention

In this example, use was made of a device of the type illustrated in FIG. 1, without a recycling loop 3, in which the reactor 1 is a 5 L stirred reactor (volume sufficient to reach equilibrium at the outlet at 80-90° C. at atmospheric pressure), and in which the distillation column, 2 is a column 3 cm in diameter comprising 30 plates and in which a vacuum of 2000 Pa (20 mbar) was established by means of a vane pump and the device 4 is a scraped-film evaporator.

In this example, the reagents were introduced with an inlet stream of 630 g/hour of methacrylic acid and an inlet stream of 370 g/hour of acetic anhydride, and also polymerization inhibitors (phenothiazine). The reaction was performed continuously in a perfectly stirred reactor whose volume is sufficient to reach equilibrium at the outlet at 80-90° C. at atmospheric pressure.

In the distillation column, the stream exiting at the bottom (crude anhydride containing 93% to 95% by mass of methacrylic anhydride and hydrated triflic acid) was 200 g/hour.

The stream of crude anhydride exiting at the bottom of the column was purified on a scraped-film evaporator, to obtain the purified anhydride.

Similar results, but with a much higher yield, are obtained when a recirculation loop such as the loop 3 of FIG. 1 attached hereto is used.

Example 2

Reactivity of Triflic Acid in Anhydrous Form and in Hydrated Form

This example illustrates the similar reactivities of triflic acid in anhydrous form and in hydrated form.

The following were introduced into a jacketed, mechanically stirred 1 liter glass reactor, maintained at 80° C. at atmospheric pressure: 150 g of acetic anhydride, 250 g of methacrylic acid, 0.8 g of phenothiazine and, depending on the test:

test 1: 25 ppm of anhydrous triflic acid
test 2: 25 ppm of triflic acid in hydrated form The reactor was kept stirring at 80° C. at atmospheric pressure and samples were taken over time, to determine the time required to reach equilibrium.

For comparative purposes: a control was performed by performing the experiment under the same conditions as tests 1 and 2, but without any addition of triflic acid.

The results obtained are reported in the table below, which shows similar results for the two forms of triflic acid:

|  | Time to reach equilibrium (in minutes) |
| --- | --- |
| Control: no triflic acid added | 140 |
| Test 1: Addition of anhydrous triflic acid (25 ppm) | 27 |
| Test 2: Addition of hydrated triflic acid (25 ppm) | 25 |

The invention claimed is:

1. A process for preparing an anhydride of formula A-C(=O)—O—(O=)C-A in which A is a group —CH=CH$_2$ or —C(CH$_3$)=CH$_2$, said process comprising:
   a) a step of reacting an anhydride B—C(=O)—O—(O=)C—B with an acid A-COOH, A being as defined above, this step leading to the formation of an anhydride A-C(=O)—O—(O=)C—B and of an acid B—COOH, A and B being such that said acid B—COOH is more volatile than said acid A-COOH; and
   b) a step of reacting said anhydride A-C(=O)—O—(O=)C—B with the acid A-COOH under conditions such that the amount of acid B—COOH is less than the amount of acid A-COOH, resulting in the formation of the anhydride A-C(=O)—O—(O=)C-A,
   in which:
      said steps (a) and (b) are performed in the presence of triflic acid in hydrated form
      the anhydride A-C(=O)—O—O(O=)C-A formed in step (b) is isolated from the reaction medium derived from step (b) according to the following successive or concomitant separation steps:
         e1) the "heavy" compounds, having a volatility less than or equal to that of the anhydride A-C(=O)—O—O(O=)C-A, are separated from said reaction medium,
         these heavy compounds including the anhydride A-C(=O)—O—(O=)C-A and triflic acid in hydrated form;
         e2) the anhydride A-C(=O)—O—O(O=)C-A is separated from the heavy compounds by difference in volatility.

2. The process as claimed in claim 1, in which the acid B—COOH is removed during the reaction steps a) and b).

3. The process as claimed in claim 1, wherein the process is performed continuously.

4. The process as claimed in claim 1, wherein the molar mass of B is less than the molar mass of A.

5. The process as claimed in claim 1, wherein B is a methyl or ethyl group.

6. The process as claimed in claim 1, in the reaction steps a) and b) are performed at a temperature of from 60° C. to 120° C.

7. The process as claimed in claim 1, in which the reaction steps a) and b) are performed at a pressure of from 0.01 bar to 3 bar.

8. The process as claimed in claim 1, comprising a step of extracting the acid catalyst and the acid B—COOH formed, in order to separate out the acid catalyst and the acid B—COOH.

9. The process as claimed in claim 8, in which the reaction steps are performed in a reactor and the extraction step is performed in one or more successive distillation columns separate from the reactor.

10. The process as claimed in claim 9, in which the reaction steps and the extraction step are performed in one or more successive distillation columns.

11. The process as claimed in claim 1, wherein, in step e1), the "heavy" compounds, having a volatility less than or equal to that of the anhydride A-C(=O)—O—O(O=)C-A, are separated from said reaction medium by fractional distillation.

12. The process as claimed in claim 5, wherein B is a methyl group.

13. The process as claimed in claim 6, in which the reaction steps a) and b) are performed at a temperature of from 70° C. to 110° C.

14. The process as claimed in claim 13, in which the reaction steps a) and b) are performed at a temperature of from 90° C. to 100° C.

15. The process as claimed in claim 7, in which the reaction steps a) and b) are performed at a pressure of from 0.5 bar to 1.5 bar.

16. The process as claimed in claim 15, in which the reaction steps a) and b) are performed at atmospheric pressure.

17. The process as claimed in claim 8, wherein the acid catalyst and the acid B—COOH formed is extracted by distillation.

* * * * *